United States Patent [19]

Pavletic

[11] Patent Number: 5,234,462
[45] Date of Patent: Aug. 10, 1993

[54] METHOD AND KIT FOR ACCELERATING THE CLOSING OF OPEN SKIN WOUNDS

[75] Inventor: Michael M. Pavletic, Hopkinton, Mass.

[73] Assignee: Tufts University, Medford, Mass.

[21] Appl. No.: 752,082

[22] Filed: Aug. 29, 1991

[51] Int. Cl.$^5$ ............................................. A61B 17/00
[52] U.S. Cl. ...................................... 606/215; 606/216
[58] Field of Search ............................ 606/213–216; 602/53, 54

[56] References Cited

U.S. PATENT DOCUMENTS

| | | | |
|---|---|---|---|
| 114,750 | 5/1871 | Battersby | 606/215 |
| 363,538 | 5/1887 | Penny | 606/215 |
| 2,421,193 | 5/1947 | Gardner | 606/215 |
| 3,402,716 | 9/1968 | Baxter | 606/215 |
| 3,559,652 | 2/1971 | Baniff | 606/214 |
| 4,646,731 | 3/1987 | Brower | 606/215 |
| 4,742,826 | 5/1988 | McLorg | 606/215 |
| 4,825,866 | 5/1989 | Pierce | 606/216 |

FOREIGN PATENT DOCUMENTS 2268504 11/1975 France .................... 606/215

Primary Examiner—Stephen C. Pellegrino
Assistant Examiner—Gary Jackson
Attorney, Agent, or Firm—Hamilton, Brook, Smith & Reynolds

[57] ABSTRACT

A method is disclosed for accelerating the stretching of skin and the closing of open skin wounds which includes the steps of attaching a plurality of anchors, which have fasteners attached to one side of the anchors, to the surface of the skin adjacent to the wound with an adhesive whereby the anchors are spaced around the wound in a manner to allow at least one strap with a plurality of fastener receivers to be positioned across the wound and the fastener receivers to be coupled to the fasteners. At least one strap with the fastener receivers is positioned across the wound. The fasteners are coupled to a plurality of the fastener receivers which are attached to at least one strap. The tension of at least one strap is adjusted to maintain sufficient tension to stretch the skin proximate to the fasteners thereby significantly accelerating wound closure.

9 Claims, 2 Drawing Sheets

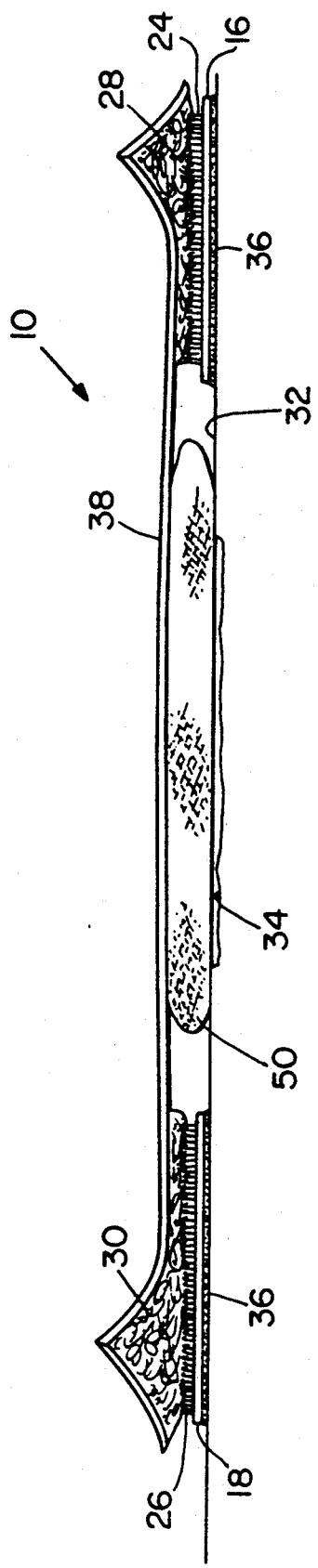
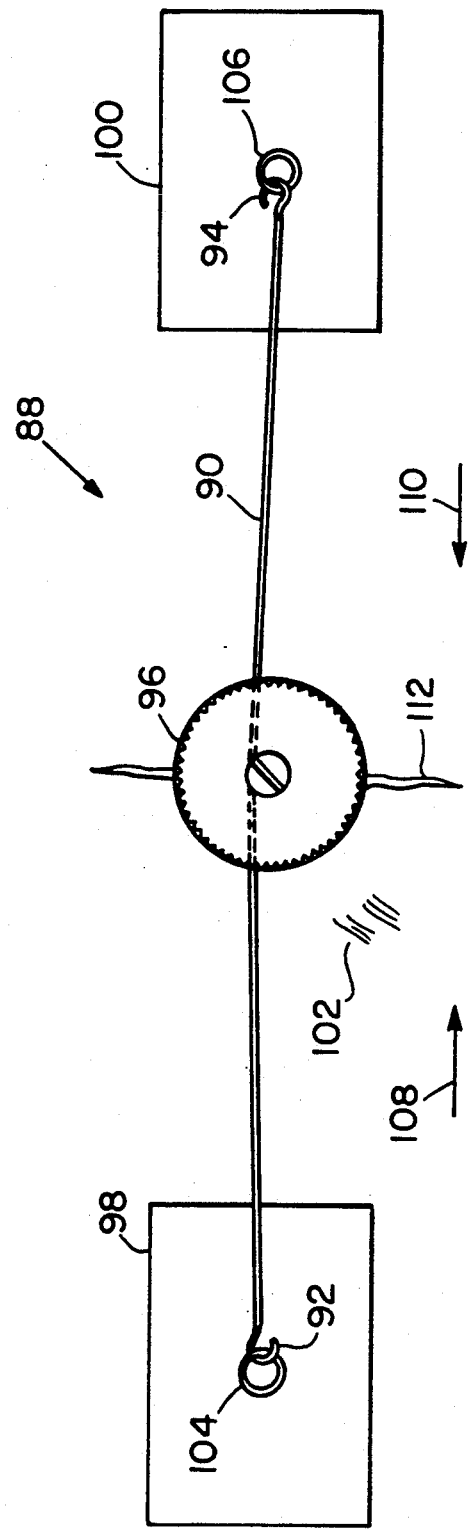
FIG. 2
FIG. 4

METHOD AND KIT FOR ACCELERATING THE CLOSING OF OPEN SKIN WOUNDS

BACKGROUND OF THE INVENTION

After skin has been wounded or burned, the opening must be closed to speed wound closure. In the cases of severe wounds or burns, there is insufficient excess skin around the sides of the defect to allow the sides to be pulled together. Similarly, when diseased or blemished cutaneous tissue is removed by surgery, insufficient skin may be left around the perimeter of the removed tissue. In the event the defect is large and cannot be easily closed, techniques have been developed for wound closure.

Two surgical techniques are skin grafts and skin flaps both of which require the elevation of skin. Skin is cut from an area near the defect or from another part of the body. This invasive surgical procedure requires anesthesia, has substantial costs and requires hospitalization. Rigid asepsis is necessary. Further, there is the risk of complications which include skin ischemia and necrosis, infection, seroma and hematoma.

Another technique is the use of skin expanders. Skin expanders are implanted under the skin and slowly inflated to expand the skin. This technique is expensive. After gradual inflation of the expander, a second surgical procedure is required to rotate or advance the skin in the form of a flap. It requires surgical implantation, anesthesia, and hospitalization. As with skin grafts, rigid asepsis is necessary. The risk of complications include infection, implant extrusion, ischemia, necrosis, scar encapsulation of the silastic implant, hematoma and/or seroma formation.

A fourth technique is presuturing where the neighboring skin is folded over the proposed surgical site with sutures temporarily prior to the surgery, to facilitate wound closure as the skin relaxes to the tension applied by the sutures. Presuturing is minimally invasive because only placement of the suture needle is required prior to the elective surgical procedure. Local anesthesia is required for suture placement. The sutures are tightened but no adjustment is possible once the sutures have been placed in the skin. The sutures can be uncomfortable. There is a small risk of infection and the sutures have a limited surface area of application for closing open wounds.

A need exists, therefore, for an improved method of accelerating the stretching of skin and open wound healing which overcomes or minimizes the above-mentioned problems.

SUMMARY OF THE INVENTION

The present invention relates to a method for accelerating the stretching of skin and the closing of open skin wounds which includes the steps of attaching a plurality of anchors, which have fasteners attached to one side of the anchors, to the surface of the skin adjacent to the wound with an adhesive, whereby the anchors are spaced around the wound in a manner to allow at least one strap with a plurality of fastener receivers to be positioned across the wound and the fastener receivers to be coupled to the fasteners. At least one strap with the fastener receivers is positioned across the wound. The fasteners are coupled to a plurality of the fastener receivers which are attached to at least one strap. The tension of at least one strap is adjusted to maintain sufficient tension to stretch the skin proximate to the fasteners thereby significantly accelerating wound closure.

A kit for accelerating the stretching of skin and the closing of open skin wounds includes a plurality of anchors, which have fasteners attached to one side of the anchors. The kit further includes an adhesive, with which the anchors are fastened to the skin adjacent to the wound, whereby the anchors are spaced around the wound in a manner to allow at least one strap with a plurality of fastener receivers to be positioned across the wound or elective surgical area and the fastener receivers to be coupled to the fasteners. The kit also includes a strap, which includes a plurality of the fastener receivers whereby when attached to the fasteners and sufficient tension is applied to the strap to sufficiently stretch the skin proximate to the anchors thereby significantly accelerating wound closure.

This invention has many advantages. The method improves the rate of open skin wound healing while not being invasive and not requiring anesthesia. The method can be used prior to an elective surgical procedure such as skin tumor removal, scar removal and removal of redundant skin, by mobilizing and stretching regional skin thereby facilitating skin closure after the surgery. The invention reduces tension on a surgical incision after closure. Sterilization is not necessary because the skin is not penetrated to attach the anchors. There is minimal pain to the patient during application and use. The straps, which hold the bandages over the wound, can be easily coupled and uncoupled for changing the bandages and wound assessment. The kit is relatively inexpensive and it can be reused.

BRIEF DESCRIPTION OF THE DRAWINGS

FIG. 2 is an end view of the embodiment of FIG. 1.

FIG. 4 is a plan view of yet another embodiment of the elements of the invention.

DETAILED DESCRIPTION OF THE INVENTION

The features and other details of the method and kit of the invention will now be more particularly described with reference to the accompanying drawings and pointed out in the claims. It will be understood that the particular embodiments of the invention are shown by way of illustration and not as limitations of the invention. The principle features of this invention can be employed in various embodiments without departing from the scope of the invention.

The present invention includes a method and kit for accelerating the closing of open skin wounds. In one illustration of the invention, shown in FIG. 1, elements 10 for accelerating the closing of an open skin wound include a series of anchors 12,14,16,18. Anchors 12,14,16,18 are made of a suitable material that can bond to an adhesive. An example of a suitable material is a synthetic fiber weaved into a fabric. In a preferred embodiment, the anchors are made of nylon.

Anchors 12,14,16,18 can be of many shapes and sizes. A suitable size and shape is one that sufficiently allows the anchors to bond with an adhesive to the skin and withstand the lateral tension from a strap. In one embodiment, the anchors are rectangular in shape with a length of about two inches and a width of about one inch.

Fasteners 20,22,24,26 are attached on anchors 12,14,16,18 by a suitable means. In one embodiment, the fasteners are sewed onto the anchors. It is also possible for the fastener and the anchor to be the same thereby being directly attached to the skin. As an example, a Velcro ® brand hook patch can be directly attached to the skin with an adhesive.

Figure 1:
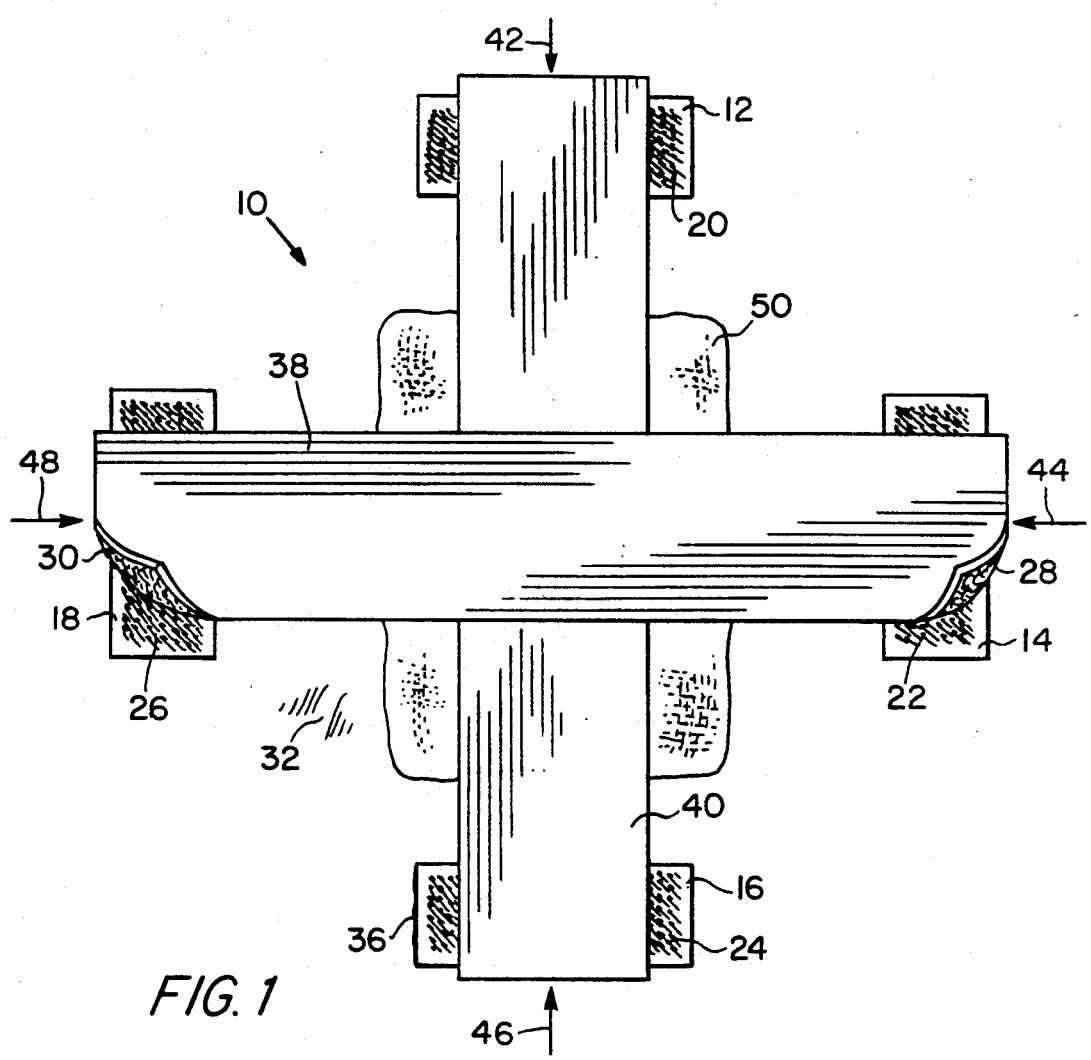
FIG. 1 is a plan view of one embodiment of the elements of this invention.

As shown in FIG. 1 and in FIG. 2, fasteners 24,26 are fastened to fastener receivers 28,30. For illustration purposes only, fastener receivers 28,30 are not fully fastened to fasteners 24,26. Fasteners 20,22 are similarly fastened to fastener receivers. The fasteners are capable of being repeatedly fastened and unfastened to the fastener receivers. Examples of fasteners and fastener receivers are snaps, clasps, and hook and eyelets. In a preferred embodiment, the fasteners and the fastener receivers are Velcro ® brand hook patches and Velcro ® brand pile patches, respectively.

Skin 32, which is a non-injured section of the dermis, is adjacent to wound 34. Wound 34 is an open wound to be closed on the surface of the dermis. The wound can be a cut, a burn, a surgical incision or another opening in the dermis that necessitates closure. Alternatively, the skin can be an area that is to be prestretched prior to surgery to allow closure of a defect caused by surgical excision of the skin. Prestretching is used to prepare skin for closing after surgery for removing diseased or blemished cutaneous tissue such as a skin tumor or scar. Wrinkled and redundant skin for cosmetic removal during plastic surgery can be prestretched.

Skin 32 is suitably prepared for attaching anchors 12,14,16,18 by removing loose particles from the surface of skin 32. An example of a suitable method includes cleaning skin 32 with soap and water or an alcohol.

Hair should be removed from skin 32 where the anchors are to be attached by a suitable method, such as by shaving. Particularly, the hair should be removed if the hair is thick. The thickness of the hair impairs the effectiveness with which an adhesive will bond the anchor to the skin. For animals with fur, such as dogs, the fur should be removed.

Anchors 12,14,16,18 are attached to skin 32 with adhesive 36. A suitable adhesive can sufficiently bond the anchors to the skin. In one embodiment, a suitable adhesive is a cyanoacrylate. In a particularly preferred embodiment, the adhesive is ethyl cyanoacrylate.

A suitable amount of adhesive 36 is placed on anchors 12,14,16,18 for bonding to skin 32. In one embodiment, an anchor with an area of two square inches requires five or six drops of ethyl cyanoacrylate spaced over the anchors. Fifteen drops is usually equal to about one milliliter. The adhesive is applied by a suitable means, such as by squeezing droplets of the adhesive from a tube.

Adhesive 36 is suitably distributed over the surface of anchors 12,14,16,18 to have sufficiently even distribution of adhesive to allow bonding to a significant portion to skin 32. Examples of a sufficiently even distribution of adhesive by which the anchors are bonded include drops, an array of drops, and a film spread over the bottom surface of the anchor prior to application to the skin.

A suitable amount of time is allowed for the adhesive to set. Typically, cyanoacrylates set quickly upon contact with air. In one embodiment, the ethyl cyanoacrylate sets within seconds of exposure to the air.

Straps 38,40 are made of a suitable material that is able to withstand the tension necessary to stretch skin in order to accelerate the closing of an open skin wound. Although two straps are illustrated, only one strap is necessary to practice the invention. A suitable strap can be of a material that is either compressive or non-compressive. In one embodiment, the straps are rubber bands. In a particularly preferred embodiment, the straps are flat ribbed elastic.

Straps 38,40 are made of a suitable size and shape. Straps 38,40 have lengths that are sufficient to cross the wound. The thicknesses and widths of the straps are sufficient to withstand the tension applied.

Fastener receivers 28,30 are attached on one side of straps 38,40. Straps 38,40 can have a plurality of fastener receivers. The applied strap tensions are maintained by adjusting straps 38,40 to fastener receivers 28,30 to stretch the skin in directions 42,44,46,48. In one embodiment, the fastener receivers are a series of snaps along one side of the strap. In a particularly preferred embodiment, the fastener receiver is a strip of Velcro ® brand pile cloth. Straps which do not have compression ability relax as the skin stretches. Straps can be adjusted periodically to tight the straps. Fasteners 20,22,24,26 and fastener receivers 28,30,32,34 allow straps 38,40 to be removed. Straps 38,40 can be easily and quickly unfastened so that bandage 50 can be removed. The underlying wound can be examined to determine the progress of healing, allows the bandage to be changed and strap fastened again. Although a bandage is used in the present example, a bandage is not necessary to practice the invention.

The tension on straps 38,40 can be adjusted as needed to maintain sufficient elastic force to continuously stretch and advance the skin toward the central area of the wound and to retain the surgical dressing against the wound. The straps are stretched sufficiently to create sufficient tension over its length between the apposed fasteners. The tension is sufficient when the skin outside the fasteners is being sufficiently stretched whereas the skin between the fasteners display laxity. Excessive tension by extreme stretching of the straps will separate the fastener from the skin. This necessitates the reapplication of glue to the anchors.

Adhesive 36 which bonds anchors 12,14,16,18 to skin 32 can be removed by a suitable solvent. In one embodiment where the adhesive is a cyanoacrylate, a suitable solvent is acetone. Another suitable method to remove anchors 12,14,16,18 is to allow anchors to naturally fall off. Typically, after about a week the top layer of skin under the adhesive naturally dies and flakes off. As the top layer of skin flakes off, anchors 12,14,16,18 will loosen and fall off.

Figure 3:
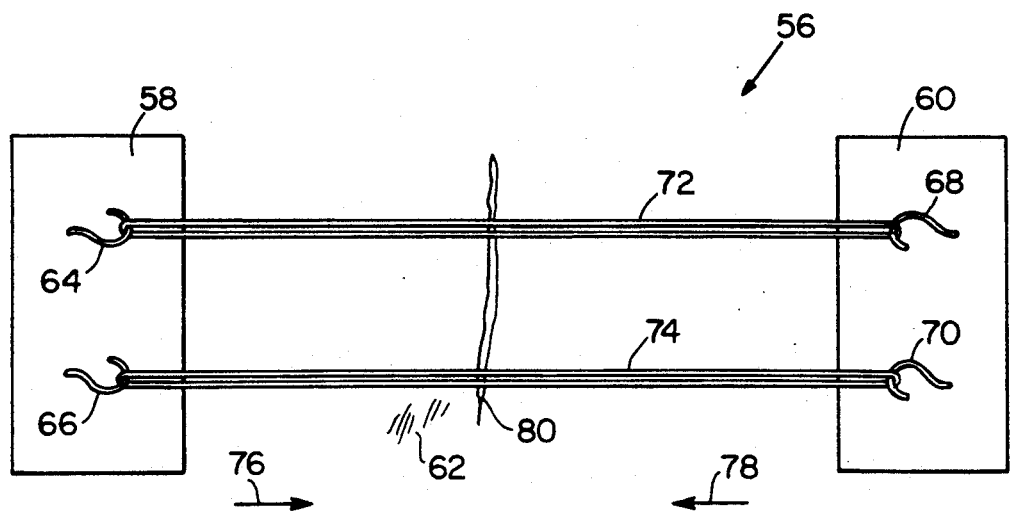
FIG. 3 is a plan view of another embodiment of the elements of the invention.

In another embodiment of the invention, shown in the FIG. 3, elements 56 include hook anchors 58,60 which are bonded to skin 62 by an adhesive. Hooks 64,66,68,70 are attached on anchors 58,60 by a suitable means such as sewing. Elastic loops 72,74 are disposed around hooks 64,66,68,70. As skin 62 stretches in directions 76,78 thereby accelerating the closing of wound 80 and the tension on elastic loops 72,74 diminishes, elastic loops can be replaced with smaller elastic loops to maintain sufficient tension.

In a further illustration of the invention, shown in the FIG. 4, skin stretcher kit 88 includes cord 90 with hooks 92,94 disposed at both ends. A suitable ratchet tightener 96 is disposed at the center of cord 90. An example of a suitable ratchet tightener has a toothed wheel and lock key. Anchors 98,100 are bonded to skin 102 by an adhesive. Eye hooks 104,106 are attached on anchors 98,100 by a suitable means. As skin stretches in directions 108,110 thereby accelerating the closing of wound 112 and the tension on skin 102 relaxes, ratchet tightener 96 is adjusted to maintain the sufficient tension.

Equivalents

Those skilled in the art will recognize, or be able to ascertain using no more than routine experimentation, many equivalents to the specific embodiments of the invention described specifically herein. Such equivalents are intended to be encompassed in the scope of the claims.

I claim:

1. A method for accelerating the stretching of skin and the closing of open skin wounds, comprising the steps of:
    a) attaching a plurality of anchors, which have fasteners attached to one side of said anchors, to the surface of the skin adjacent to the wound with an adhesive, whereby said anchors are spaced around the wound in a manner to allow at least one elastomeric strap with a plurality of fastener receivers to be positioned across the wound and said fastener receivers to be coupled to said fasteners;
    b) positioning at least one elastomeric strap with said fastener receivers across the wound;
    c) coupling said fasteners to a plurality of said fastener receivers which are attached to at least one elastomeric strap; and
    d) adjusting periodically the tension of at least one elastomeric strap to maintain sufficient tension to stretch the skin proximate to said fasteners, thereby significantly accelerating wound closure.

2. A method of claim 1 wherein the adhesive is a cyanoacrylate.

3. A method of claim 2 wherein the anchors are nylon cloth.

4. A method of claim 3 wherein the fasteners comprise hook pads.

5. A method of claim 4 wherein the fastener receivers comprise pile pads.

6. A kit for use in accelerating the closing of open skin wounds, comprising:
    a) a plurality of anchors, which have hook pad fasteners attached to one side of said anchors;
    b) a cyanoacrylic adhesive, for fastening said anchors to the skin adjacent to the wound; and
    c) a flat ribbed elastomeric strap which includes a plurality of pile pad fastener receivers.

7. A kit of claim 6 wherein the anchors are nylon cloth.

8. A method for stretching skin prior to surgery to allow closure of a defect caused by surgical excision of the skin, comprising the steps of:
    a) attaching prior to surgery a plurality of anchors, which have fasteners attached to one side of said anchors, to the surface of the skin adjacent to an excision area with an adhesive, whereby said anchors are spaced around the excision area in a manner to allow at least one elastomeric strap with a plurality of fastener receivers to be positioned across the excision area and said fastener receivers to be coupled to said fasteners;
    b) positioning at least one elastomeric strap with said fastener receivers across the excision area;
    c) coupling said fasteners to a plurality of said fastener receivers which are attached to at least one elastomeric strap; and
    d) adjusting the tension of at least one elastomeric strap to maintain sufficient tension to stretch the skin proximate to said fasteners, thereby significantly stretching the skin prior to surgery in order to prepare skin for closing after surgery.

9. A kit for use in accelerating the closing of open skin wounds, comprising:
    a) a plurality of anchors, which have fasteners attached to one side of said anchors;
    b) an adhesive, for fastening said anchors to the skin adjacent to the wound;
    c) a cord, which has a plurality of fastener receivers; and
    d) a ratchet tightening means, which is disposed on said cord.

* * * * *